United States Patent [19]

Kirsch

[11] Plant 5,199

[45] Mar. 6, 1984

[54] LILY NAMED ROSARIO

[75] Inventor: Ted T. Kirsch, Myrtle Point, Oreg.

[73] Assignee: Sun Valley Bulb Farms, Inc., Myrtle Point, Oreg.

[21] Appl. No.: 421,901

[22] Filed: Sep. 23, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Chas. W. Rummler

[57] ABSTRACT

A new and distinct lily cultivar of the Parkmanni type Oriental hybrid, particularly distinguished by its large light pink outwardly facing flowers, having slightly recurved petals with numerous reddish spots on the inner half of the petal length, on each side of the inner portion of the mid-rib, the flowers being borne in a raceme arrangement each on a long strong outwardly projecting pedicel; and the plant having dark green and relatively disease-resistant foliage.

2 Drawing Figures

BACKGROUND OF THE NEW PLANT

This new variety of lily plant originated as a seedling of unknown parentage growing in nursery at Arcata, Calif., this plant being selected by me for propagation and study because of its large pink outwardly facing attractive flowers and plant form. Propagation of this lily under my direction through successive generations by means of scales and tissue culture at Arcata, Calif. has shown that this plant has very advantageous and distinctive characteristics which make it a valuable addition to the commercial field of cut flower lily culture; and continued propagation of this new plant has shown that the distinctive characteristics of this plant hold true from generation to generation and appear to be firmly fixed.

DESCRIPTION OF THE DRAWING

This new lily cultivar is illustrated by the accompanying photographic drawing which in full color shows a full grown blooming plant and a closeup view of several blooms comprising the flowering head of the main stem, the color rendition being as nearly true as can be obtained by conventional photographic procedures.

DESCRIPTION OF THE PLANT

The following is a detailed description of my new lily cultivar with color designations according to the R.H.S. Colour Chart published by The Royal Horticultural Society of London, England, the observations having been made on greenhouse grown plants at Arcata, Calif. in the spring of 1982.

THE PLANT

Origin: Seedling.

Parentage: Unknown.

Classification:

*Botanic.*—Oriental Hybrid, Parkmanni type.

*Commercial.*—Lily for cut flower production.

Form: A tall single stem arising from each single nose bulb.

Height: From 2 to about 3½ feet.

Growth habit: Sturdy and upright with excellent strength.

Cane diameter: About ¼ inch from a small bulb to about ½ inch from a large bulb.

Foliage:

*Leaves.*—At flower cluster — 2 in number, 1 at the base of each pedicel and 1 on the pedicel about 1 to 1½ inches from the flower, these leaves being about 4½ to 5 inches long and about 1 inch wide.

*Shape.*—Linear. (Some leaves may be lanceolate.)

*Texture.*—Leathery.

*Aspect.*—Smooth.

*Ribs and veins.*—The leaves have distinct longitudinal veins extending from base to tip.

Bulblets: (On underground stem)

*Occurrence.*—1 to 3 on each healthy normal plant at digging time.

*Size.*—From about ¼ inch to 1 inch in diameter.

*Color.*—White, with occasional pink shading at the tips.

Bulbs:

*Size.*—Up to about 12 inches in circumference depending upon age.

*Color.*—White, with yellow and pink overtones. As the bulbs become larger and older, the overtones of yellow and pink become more and more prominent.

THE BUD

Form: Elliptic with acute apex.

Size: About 4 to 4½ inches long and about 1¼ to 1½ inches wide.

Number: Usually 1 on each pedicel, the main stem having from 1 to 6 pedicels with buds according to culture and bulb size.

Opening rate: Normal; the buds open successively from the lowermost bud to the top bud which is the last to open.

Color: In general, light pink, light green along the mid-rib at the base and at the apex at the time the sepals first divide and the petals begin to unfurl.

Surface texture: Rugose, and leathery with prominent veins.

Pedicels:

*Character.*—Strong and generally outwardly projecting at an angle of about 60° from the stem.

*Color.*—Light green with some maroon coloration between the base and the second leaf on the pedicel.

*Aspect.*—Glabrous and glaucous.

*Length.*—About 2 to 4 inches.

THE FLOWER

Blooming habit: This plant blooms annually and profusely in early June outdoors.

Size of flower: Large, about 6 to 7 inches in diameter.

Borne:

*From large bulbs.*—The inflorescence has a raceme arrangement, and there may be from 3 to 4 blooms open at one time. The size of the bulb and its cultural care will determine the number of blooms and buds to be found in a normal inflorescence.

Shape of flower: Saucer-shaped with uniformly shaped petals in a star arrangement, the outer third of each petal being recurved.

Petalage: Normal, 3 sepals and 3 petals.

*Form.*—Ovate with a central furrow bisecting each petal and sepal longitudinally with the edges of the blade being slightly undulate, the petals having an obtuse apex and the sepals having an acute apex.

*Size.*—Petals and sepals are about 4 inches long and about 2⅛ inches wide.

*Texture.*—Leathery.

*Aspect.*—Velvety.

*Color.*—When grown indoors on the West Coast States: Upper side: Upon opening the petals are R.H.S. Red Purple 62-C, the outer edges being slightly lighter and the color being darker toward the mid-rib. The bottom half of each petal is covered with numerous maroon spots. The base of the mid-rib of both petals and sepals is green turning to a light yellow green and then to a darker pink. The sepals are slightly darker in color and have few or no spots. Under side: R.H.S. 56-A. The base of the mid-rib is light green or pink, turning to a darker pink until half way up the petal where the mid-rib is of normal color.

*Papillae.*—Present on petals and from 4 to 8 in number.

Fragrance: Sweet.

Discoloration: The color darkens somewhat as the blossom matures.

Effect of weather: Generally, the flowers are not affected by wet weather, but the flower ages as temperature rises.

Persistence: The flower tends to hang on and dry.

Lasting quality:

*On the plant.*—2 to 3 weeks depending on the size of the bulb and its environmental temperature.

*As a cut flower.*—10 to 14 days.

REPRODUCTIVE ORGANS

Stamens:

*Number.*—6. Orderly arranged around the pistil.

*Anthers.*—Length — ⅝ inch. Color: R.H.S. 25-A.

*Filaments.*—Length — About 2½ inches. Color: White at base to light green at anthers.

Pistil: Number — 1.

*Style.*—Length about 2 inches.

*Stigma.*—Light green with some purple spots along the edges.

Ovary: About 1 inch long and 1 inch wide at maturity; classified as a schizocarp, dehiscing into thirds and containing 6 rows of seeds of the usual shape for lilies.

I claim:

1. A new and distinct Oriental hybrid lily cultivar, substantially as herein shown and described, characterized by its large pink outwardly facing flowers, the petals of which are recurved slightly and have numerous maroon spots on the basal half, the flowers being borne on strong still outwardly projecting pedicels and the blooms being long lasting whether on the plant or as cut flowers.

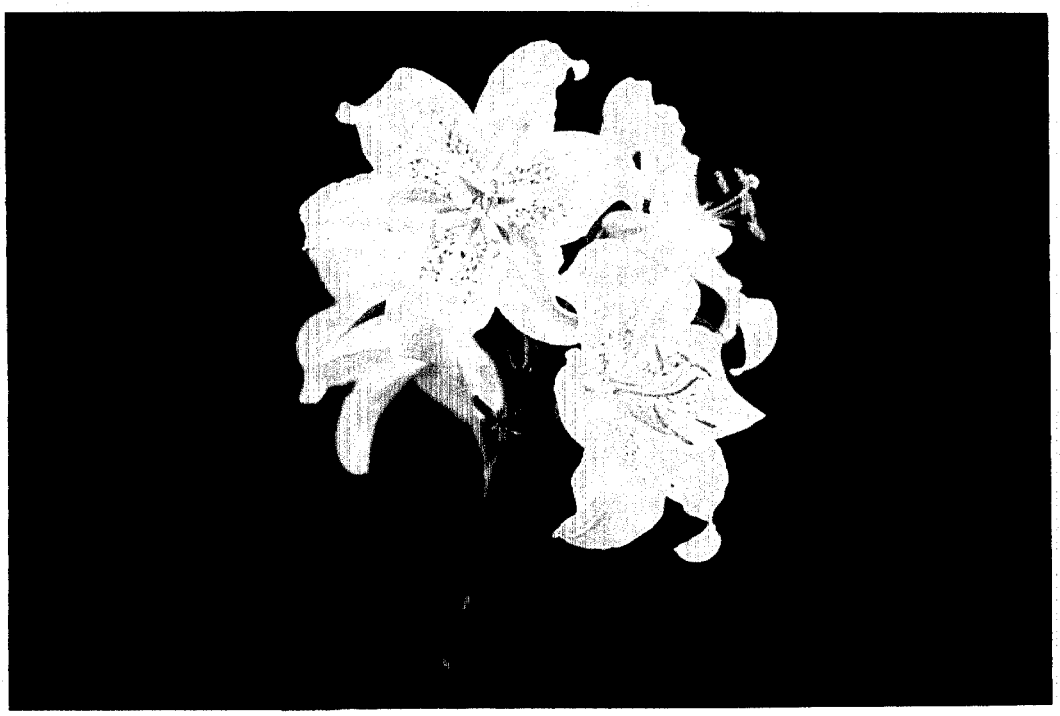
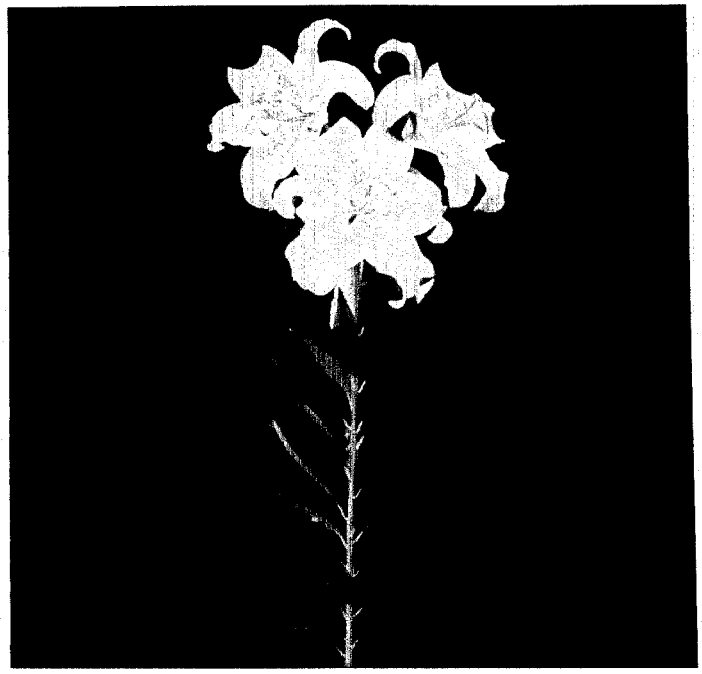

* * * * *